United States Patent [19]

Warriner

[11] Plant 5,118

[45] Oct. 11, 1983

[54] ROSE PLANT JACMAT

[75] Inventor: William A. Warriner, Tustin, Calif.

[73] Assignee: Jackson & Perkins Company, Medford, Oreg.

[21] Appl. No.: 353,022

[22] Filed: Mar. 1, 1982

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Klarquist, Sparkman, Campbell, Leigh, Whinston & Dellett

[57] ABSTRACT

A miniature rose variety having a plant which reaches only 2 feet in height in one year; orange-red flower color; stiff petals causing flower form to be retained through aging.

1 Drawing Figure

This present invention relates to a new and distinct variety of rose plant of the miniature class which was originated by me by crossing the variety Zorina, U.S. Plant Pat. No. 2,381, with the variety Fire Princess, U.S. Plant Pat. No. 3,084.

The primary objective of this breeding was to produce a new rose variety combining the coloring of Zorina and the miniature plant and stiff petals of Fire Princess. This objective was substantially achieved along with other desirable improvements as evidenced by the following unique combination of characteristics which are outstanding in the new variety and which distinguish it from its parents, as well as from all other varieties of which I am aware:

1. A miniature plant reaching only 2 feet in height in one year.
2. Flower color of orange-red.
3. Stiff petals causing the flower form to be retained until aging is complete.

Asexual reproduction of this new variety by cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Zorina, U.S. Plant Pat. No. 2,381.

*Pollen parent.*—Fire Princess, U.S. Plant Pat. No. 3,084.

Classification:

*Botanical.*—Rosa hybrid.

*Commercial.*—Miniature.

FLOWER

Observations made from specimens grown at Irvine, Calif. in November.

Blooming habit: Continuous.

Bud:

*Size.*—$\frac{1}{2}''$ when petals start to unfurl.

*Form.*—Pointed ovoid.

*Color.*—When sepals first divide, Orange-Red 34A. When half blown, upper side of petals Orange-Red 34A; lower side of petals Orange-Red 34A.

*Sepals.*—Color: Outer surface partly Green 138A, mostly overlaid with Greyed Purple 183A, smooth with a few glands. Three appendaged sepals normally appendaged. Two unappendaged sepals hairy edged.

*Receptacle.*—Color: Green 138A, overlaid with Greyed Purple 183A. Shape: Apple. Size: Large. Surface: Smooth.

*Peduncle.*—Length: Short. Surface: Glandular. Color: Light green, bronzy. Strength: Stiff, heavy.

Bloom:

*Size.*—Small. Average open size is $1\frac{3}{4}''$.

*Borne.*—In clusters, flat.

*Stems.*—Short, strong.

*Form.*—When first open, flat. Permanence: Retains its form to the end.

*Petalage.*—Number of petals under normal conditions, 27–30.

*Color.*—Center of flower: Upper side of petals Orange-Red 34A; reverse side of petals Red 43C; base of petals near white when fully open, yellow in bud stage. General tonality from a distance Orange-Red 34A.

*Variegations.*—Occasionally 1 or 2 outer petals formed as a sepal.

*Discoloration.*—General tonality at end of first day: slight fading. Third day: fading to Orange-Red 34B and C.

*Fragrance.*—None.

Petals:

*Texture.*—Thick, rigid.

*Shape.*—Obovate.

*Form.*—Edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large, many. Color: Yellow. Arrangement: Regular around styles.

*Filaments.*—Color: Reddish.

*Pollen.*—Gold yellow.

*Styles.*—Color: White.
*Stigmas.*—Color: Red.

PLANT

Form: Bush.
Growth: Vigorous, dwarf, branching. Grows to approximately 2 feet first year.
Foliage: Number of leaflets on normal mid-stem leaves: 5–7.
*Size.*—Small.
*Quantity.*—Normal.
*Color.*—New foliage: Greyed Purple 183A. Old foliage: Green 139A above, Green 139B lower side.
Leaflets:
*Shape.*—Oval pointed.
*Texture.*—Upper side: Leathery.
*Edge.*—Serrated.
*Serration.*—Single, small.
Petiole.—Rachis: Color: Green. Underside: Prickles.

*Stipules.*—Long, bearded.
*Disease resistance.*—Resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main stalks from base, many. On laterals from stalk, many.
*Form.*—Long, hooked slightly downward.
*Color when young.*—Brown.
*Position.*—Irregular.
Small prickles:
*Quantity.*—On main stalks, none. On laterals, none.

I claim:

1. A new and distinct variety of rose plant of the miniature class, substantially as herein shown and described, characterized particularly as to novelty by the unique combination of its compact habit of growth, stiff flowers of orange-red.

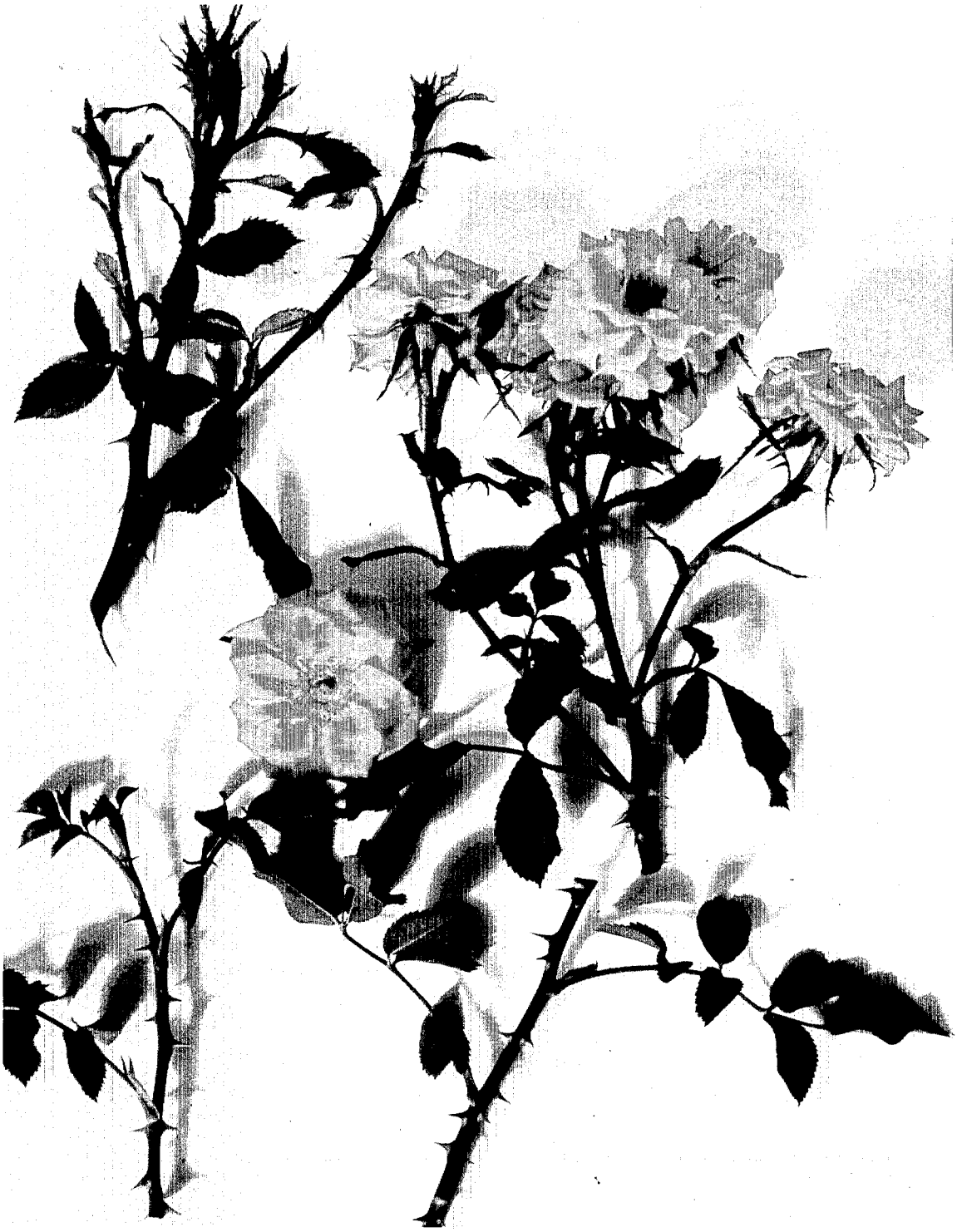

* * * * *